United States Patent [19]

Poirier

[11] Patent Number: 5,118,325
[45] Date of Patent: Jun. 2, 1992

[54] AMINOFULVENE DERIVATIVES AS ANTIKNOCK COMPOUNDS

[75] Inventor: Marc A. Poirier, Clearwater, Canada

[73] Assignee: Exxon Research and Engineering Company, Florham Park, N.J.

[21] Appl. No.: 636,529

[22] Filed: Dec. 31, 1990

[51] Int. Cl.$^5$ .......................................... C10M 133/16
[52] U.S. Cl. ...................................... 44/399; 44/304; 44/340; 44/412
[58] Field of Search .................. 44/304, 340, 399, 412

[56] References Cited

U.S. PATENT DOCUMENTS 3,706,541 12/1972 Stournas et al. ...................... 44/340

Primary Examiner—Brian E. Hearn
Assistant Examiner—Maria Nuzzolillo
Attorney, Agent, or Firm—John W. Ditsler

[57] ABSTRACT

Certain aminofulvene derivatives are effective in improving the antiknock performance of gasoline when used in an internal combustion engine. Particularly preferred aminofulvene derivatives are 2-methoxycarbonyl-6-(dimethylamino)fulvene; 2,3-dimethoxycarbonyl-6-(dimethylamino)fulvene; or mixtures thereof.

14 Claims, No Drawings

AMINOFULVENE DERIVATIVES AS ANTIKNOCK COMPOUNDS

BACKGROUND OF THE INVENTION

1. Field of the Invention

This invention concerns a gasoline composition having improved antiknock performance in an internal combustion engine due to the presence of certain aminofulvene derivatives.

2. Description of Related Art

The current and most inexpensive method for improving the antiknock quality of gasoline is to add one or more organometallic antiknock compounds. In the past, tetraalkyl lead compounds (more specifically tetraethyl lead) have been one of the most effective antiknock additives. However, lead compounds are being phased out because of environmental concerns related to their high toxicity. This has prompted the need to develop acceptable antiknock additives that are lead-free.

Numerous organometallic compounds possessing antiknock activity have been proposed to replace tetraethyl lead. For example, methylcyclopentadienyl manganese tricarbonyl (MMT) is known to be an effective antiknock additive (see U.S. Pat. Nos. 2,818,417; 2,839,552; and 3,127,351), and is currently used in unleaded fuels in Canada and in leaded gasoline in the U.S.

Numerous non-metallic (i.e. ashless) compounds have also been suggested as antiknock additives. Examples of such ashless compounds include 1,4 and 1,3-diaminobutanes (see U.S. Pat. No. 4,445,909), 2 -dimethylamino methyl-4-fluorophenol (see U.S. Pat. No. 4,378,231), norbornadiene (see U.S. Pat. No. 4,387,257), and alkyl carbonates (see U.S. Pat. No. 4,600,408). Particularly preferred ashless antiknock compounds are aniline and certain of its alkyl derivatives such as 2,6-dimethylaniline, n-methylaniline, n-alkyl toluidines (see U.S. Pat. No. 4,294,587), and o-aminoazides (see U.S. Pat. No. 4,266,947). However, ashless compounds have never been commercialized because of one or more debits such as high cost, relatively low antiknock quality, hydrolytic, thermal or oxidative instability, low solubility in gasoline, or high solubility in water.

Various fulvene derivatives have also been suggested as antiknock additives. For example, U.S. Pat. No. 4,264,336 discloses the use of halogenated fulvenes as antiknock compounds. However, the use of chloro or fluoro hydrocarbons an antiknock agents may be environmentally undesirable due to their detrimental effect on the ozone layer. In addition, U.S. Pat. No. 3,706,541 discloses the use of certain aminofulvenes [such as 6-dimethylamino fulvene]as antiknock additives. More recently, 6-dimethylamino fulvene has been reported to be among the most active non-metallic antiknock additives (see S. Stournos et 199th National ACS Meeting, Boston, Mass., April 22, 1990).

However, none of these patents and publications suggest that the particular class of ashless aminofulvene derivatives disclosed herein is effective in improving the antiknock performance of gasoline.

SUMMARY OF THE INVENTION

This invention concerns a gasoline composition containing a particular class of fulvene derivatives. More specifically, I have discovered that gasoline containing a minor amount of certain oil soluble aminofulvene derivatives (or their mixtures) can improve the antiknock performance of the gasoline when used in an internal combustion engine. Preferred aminofulvenes are 2-alkoxycarbonyl-6-(dimethylamino)-fulvene; 2-3-dialkoxycarbonyl-6-(dimethylamino)fulvene, or mixtures thereof. Preferably, the alkoxy group is methoxy or ethoxy, with methoxy being most preferred.

DETAILED DESCRIPTION OF THE INVENTION

The aminofulvene derivatives used as anti-knock additives in this invention may be characterized by any one of the following formulas:

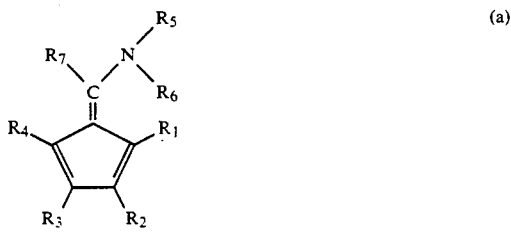
(a)

wherein $R_1$-$R_4$ may be hydrogen provided that one or two of $R_1$-$R_4$ is an electron withdrawing group selected from the group consisting of CHO, $COR_8$, $COOR_8$, CN, and $NO_2$ where $R_8$ is a hydrocarbyl group having from 1 to 8 carbon atoms, $R_5$ and $R_6$ are each a hydrocarbyl group containing from 1 to 8 carbon atoms, $R_7$ is hydrogen, a hydrocarbyl group having 1 to 8 carbon atoms, or

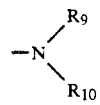

where $R_9$ and $R_{10}$ are each an alkyl group having from 1 to 8 carbon atoms; or

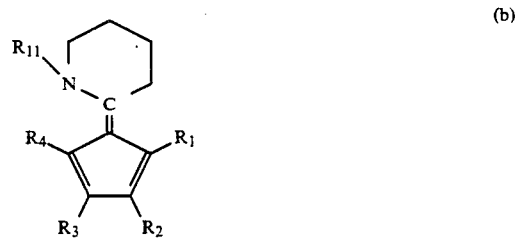
(b)

where $R_1$-$R_4$ are each hydrogen or an electron withdrawing group selected from the group consisting of CHO, $COR_8$, $COOR_8$, CN, and $NO_2$ where $R_8$ is a hydrocarbyl group having from 1 to 8 carbon atoms, $R_{11}$ is an alkyl group having from 1 to 8 carbon atoms; or (c)

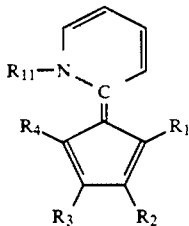

where $R_1$-$R_4$ and $R_{11}$ are defined as in (b) above.

For structure (a), any of $R_1$-$R_4$ may be hydrogen provided that one or two of $R_1$-$R_4$ is an electron withdrawing group selected from the group consisting of $CHO$, $COR_8$, $COOR_8$, $CN$, and $NO_2$. Possible arrangements include $R_2$=$R_3$=$R_4$=H, $R_1$=CHO, $COR_8$,$COOR_8$,CN, or $NO_2$ $R_1$=$R_3$=$R_4$=H, $R_2$=CHO, $COR_8$,$COOR_8$,CN, or $NO_2$ $R_1$=$R_4$=H, $R_2$=$R_3$=$COR_8$,$COOR_8$,CN, or $NO_2$ $R_2$=$R_3$=H, $R_1$=$R_4$=$COR_8$,$COOR_8$,CN, or $NO_2$ $R_4$=H, $R_1$=$R_2$=$R_3$=CHO, $COR_8$,$COOR_8$,CN, or $NO_2$ where $R_8$ is a hydrocarbyl group having from 1 to 8, preferably from 1 to 2, carbon atoms. $R_8$ can be alkyl, aryl, alkylaryl, or arylalkyl, but is preferably a straight chained (or linear) alkyl group. Examples of $R_8$ include hydrocarbyl groups such as methyl, ethyl, propyl, iso-propyl, n-butyl, iso-butyl, tert-butyl, phenyl, benzyl, and the like. Most preferably, $R_8$ is a methyl group.

$R_5$ and $R_6$ are each a hydrocarbyl group containing from 1 to 8 carbon atoms. The hydrocarbyl group may be linear, branched, or cyclic, but should be saturated. Examples of $R_5$ and $R_6$ are methyl, ethyl, propyl, iso-propyl, n-butyl, iso-butyl, tert-butyl groups, and the like. $R_5$ and $R_6$ may be the same or different. Preferably, $R_5$ and $R_6$ are methyl or ethyl groups. Most preferably, both $R_5$ and $R_6$ are each a methyl group.

$R_7$ is hydrogen, a hydrocarbyl group having from 1 to 8 carbon atoms, or

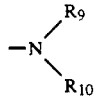

where $R_9$ and $R_{10}$ are each a alkyl group having from 1 to 8 carbon atoms, such as methyl, ethyl, propyl, iso-propyl, n-butyl, iso-butyl, tert-butyl, and the like. $R_9$ and $R_{10}$ may be the same or different, and may be linear or branched, with linear being preferred. Preferably, $R_9$ and $R_{10}$ are methyl or ethyl groups. Most preferably, $R_9$ and $R_{10}$ are each a methyl group.

If $R_7$ is a hydrocarbyl group, $R_7$ can be alkyl, aryl, alkylaryl, or arylalkyl, but preferably is a linear alkyl group. Examples of $R_7$ include hydrocarbyl groups such as methyl, ethyl, propyl, iso-propyl, n-butyl, iso-butyl, tert-butyl, phenyl, benzyl, and the like. If a hydrocarbyl group, $R_7$ is preferably a methyl or ethyl group, with methyl being more preferred. Preferably $R_7$ is hydrogen or a methyl group, with hydrogen being most preferred.

Preferred compounds having structure (a) are 2-methoxycarbonyl-6-(dimethylamino)fulvene; 2,3-dimethoxycarbonyl-6-(dimethylamino)fulvene; or mixtures thereof.

For structures (b) and (c), any one of $R_1$-$R_4$ can be hydrogen or one of the electron withdrawing groups defined for structure (a) above. $R_1$-$R_4$ can be the same or different. $R_{11}$ is a alkyl group containing from 1 to 8, preferably from 1 to 2, carbon atoms. Preferably, $R_{11}$ is a linear alkyl group. Most preferably, $R_{11}$ is a methyl group.

Examples of effective antiknock compounds that correspond to the above general formula include:

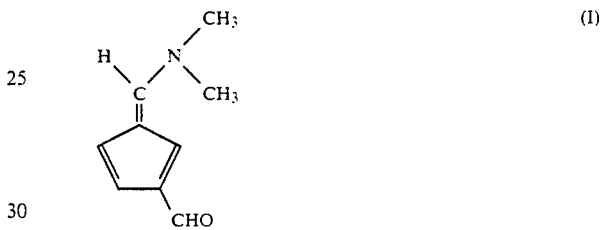

where $R_1$=$R_3$=$R_4$=$R_7$=H
$R_2$=CHO
$R_5$=$R_6$=$CH_3$

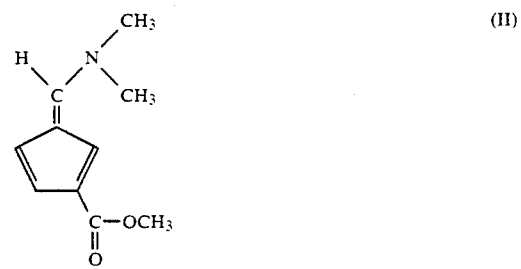

where $R_1$=$R_3$=$R_4$=$R_7$=H
$R_2$=$COOCH_3$
$R_5$=$R_6$=$CH_3$
6,6-(dimethylamino) fulvene

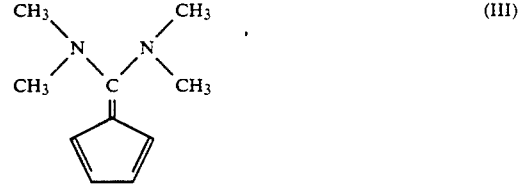

where $R_1$=$R_2$=$R_3$=$R_4$=H
$R_5$=$R_6$=$CH_3$
$R_7$=$R_9NR_{10}$
$R_9$=$R_{10}$=$CH_3$ 2-cyclopentadienylidene-1-methyl-1,2-dihydropyridine (IV)

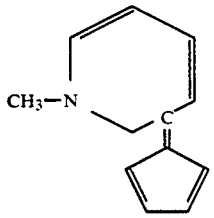

where $R_1=R_2=R_3=R_4=H$
$R_{11}=CH_3$ 2,3-dimethoxycarbonyl-6-(dimethylamino) fulvene (V)

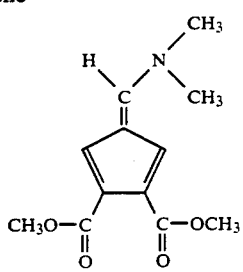

where $R_1=R_4=R_7=H$
$R_2=R_3=COOCH_3$
$R_5=R_6=CH_3$

Compounds II and V are the most preferred compounds.

The gasoline compositions of this invention will, in general, comprise a major amount of gasoline and a minor amount of the aminofulvene derivatives described above. However, the precise amount of aminofulvene derivatives used can vary broadly. As such, only an amount effective or sufficient to improve the antiknock performance of the fuel need be used. Typically, however, the amount of aminofulvene derivatives used will range from about 25 to about 2500 mg/liter, although greater amounts could be used. Preferably, from about 50 to 1000, more preferably from about 50 to about 400, mg/liter of the aminofulvene derivatives will be present in the fuel. The gasoline can contain n-paraffins, iso-paraffins, naphthenes, olefins, and aromatic compounds, or any mixture of such hydrocarbons obtainable from straight run naphtha, thermally or catalytically cracked hydrocarbon streams, or from reformer and alkylation streams.

Aminofulvenes without any electron withdrawing groups on the cyclopentadiene ring can be prepared by methods well known in the art. For example, Organic Synthesis, 47, p 52 (1967) discloses a method for preparing the complex

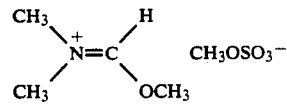

by reacting N,N-dimethylformamide with dimethyl sulphate and then reacting this complex with cyclopentadienylsodium to produce the 6-dimethylamino fulvene (V). Grundke and Hoffmann [J. Org. Chem., 46, p. 5428 (1981)] also describe another method for preparing 6-dimethylamino fulvene b reacting cyclopentadiene with dimethylacetamide dimethyl acetal in tetrahydrofuran (THF) at room temperature.

Hart et al. [J. Am. Chem. Soc., 102, p. 1196 (1980)] describe a general method for adding electron withdrawing groups to the cyclopentadiene ring, which method is illustrated below:

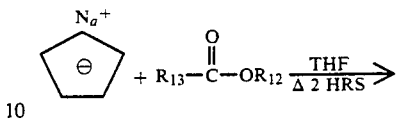

where $R_{12}$ is $CH_3$, $C_2H_5$, or phenyl; $R_{13}$ is hydrogen, $R_8$, or $OR_8$; and $R_5$, $R_6$, $R_7$, and $R_8$ are as defined previously.

Other additives may be included in the gasoline. Examples of such additives include other antiknock agents (e.g. MMT), detergents, dispersants, demulsifiers, antioxidants, anticorrosives, dyes, deicers, intake valve deposit control additives, antistatic additives, stabilizers, oxygenates such as MTBE, and the like.

Although the aminofulvene derivatives used herein will generally be added directly to gasoline, they may be formulated as a concentrate using a hydrocarbon solvent, an ether solvent, or mixtures thereof boiling in the range of about 150° to about 400° F. Preferably, an aromatic hydrocarbon solvent (such as benzene, toluene, xylene, or higher boiling aromatics or aromatic thinners, and the like) is used. Aliphatic ethers of about 3 to 8 carbons atoms (such as methyltertiary butyl ether (MTBE), ethyltertiary butyl ether (ETBE), and the like), alone or in combination with hydrocarbon solvents, can also be used with the aminofulvene derivatives. The amount of the aminofulvene derivatives in the concentrate will ordinarily be at least about 5 wt. % and, generally, will not exceed about 10 wt. %. Similarly, the amount of hydrocarbon solvent will typically range from about 90 to about 95 wt. % of the concentrate.

The gasoline compositions of this invention (including the concentrate) may also contain a small amount (typically from about 0.02 to about 0.5 wt. % and preferably from about 0.02 to about 0.15 wt. %) of a carrier fluid of low volatility. As used herein, the term "carrier fluid" is meant to include hydrocarbon and oxygenated species. Typically, the carrier fluid will have a kinematic viscosity of between about 5 to about 500 cSt at 100° C. Examples of such carrier fluids include lubricating oil base stocks, alcohols, polyols, polyol esters, polyalkyleneoxides (e.g. Ucon® Fluids available from Union Carbide), their mixtures, and the like.

This invention will be further understood by reference to the following Example, which includes a preferred embodiment of this invention, but is not intended to reduce the scope of the claims appended hereto.

EXAMPLE

Effectiveness of Aminofulvenes in Improving Antiknock Performance

The antiknock performance of several gasoline samples was determined by measuring the Research Octane Number (RON) and the Motor Octane Number (MON) of each sample. The samples tested contained the aminofulvene derivaties of this invention, conventional octane extenders (toluene and MTBE), other classes of ashless antiknock compounds (aromatic amines such as O-toluidine and 2,6-dimethylaniline), or other aminofulvenes. The base gasoline used in these tests had the following properties:

| D86 Distillation, °C. | |
|---|---|
| IBP | 28 |
| 5% | 38 |
| 10% | 43 |
| 20% | 55 |
| 30% | 70 |
| 40% | 85 |
| 50% | 98 |
| 60% | 109 |
| 70% | 124 |
| 80% | 142 |
| 90% | 171 |
| 95% | 183 |
| FBP | 183 |
| Sulfur, mg/l | 110 |
| Saturates, vol % (FIA) | 67.8 |
| Olefins, vol % (FIA) | 9.1 |
| Aromatics, vol % (FIA) | 23.1 |
| Lead, mg/l | 0 |
| Manganese, mg/l | 0.3 |
| RON | 92.4 |
| MON | 84.4 |
| (RON + MON)/2 | 88.4 |

The results of these tests as shown in Table 1 below.

antiknock compounds relative to conventional octane extenders (Runs 1 and 2), ashless antiknock compounds (Runs 3-6), and other aminofulvenes (Runs 7-9). In particular, additives having structure II, structure IV, and a combination of structures IV and V show significantly better results at lower concentrations than the compounds in Runs 1-9.

What is claimed is:

1. A gasoline composition comprising
   (a) a major amount of gasoline and
   (b) a minor amount of an aminofulvene derivative having any one of the following formulas:

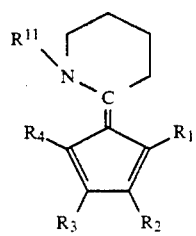

(i)

where $R_1$-$R_4$ are each hydrogen or an electron withdrawing group of the formula $COOR_8$, where $R_8$ is a hydrocarbyl group having from 1 to 8 carbon atoms, $R_{11}$ is an alkyl group having from 1 to 8 carbon atoms;

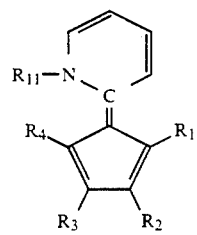

(ii)

where $R_1$-$R_4$ and $R_{11}$ are defined as in (i) above, or
(iii) mixutres thereof.

2. The composition of claim 1 wherein $R_8$ is a linear alkyl group.

TABLE 1

| Run | Additive | Treat Rate mg/l | ΔRON | ΔMON | Δ(RON + MON)/2 |
|---|---|---|---|---|---|
| 1 | toluene | 35,000 (4 vol %) | +1.0 | +0.3 | +0.65 |
| 2 | MTBE | 30,320 (4 vol %) | +1.0 | +0.5 | +0.75 |
| 3 | O-toluidine | 1,000 | +0.1 | 0 | +0.05 |
| 4 | O-toluidine | 3,600 | +0.8 | +0.3 | +0.55 |
| 5 | 2,6-dimethylaniline | 1,000 | +0.3 | +0.2 | +0.25 |
| 6 | 2,6-dimethylaniline | 3,500 | +1.0 | +0.7 | +0.85 |
| 7 | 6-dimethylamino fulvene | 500 | +0.3 | +0.1 | +0.20 |
| 8 | 6-dimethylamino fulvene | 1,000 | +0.6 | +0.2 | +0.40 |
| 9 | 6-dimethylamino fulvene | 1,500 | +0.7 | +0.4 | +0.55 |
| 10 | Structure III | 500 | +0.3 | +0.1 | +0.20 |
| 11 | Structure III | 1,000 | +0.5 | +0.3 | +0.40 |
| 12 | Structure II | 400 | +0.6 | +0.3 | +0.45 |
| 13 | Structure II | 1,000 | +0.5 | +0.6 | +0.55 |
| 14 | Structure IV | 190 | +0.5 | +0.2 | +0.35 |
| 15 | Structure IV | 370 | +1.0 | +0.2 | +0.60 |
| 16 | Structures II + V | 90 | +0.6 | +0.2 | +0.4 |
| 17 | Structures II + V | 195 | +0.9 | 0 | +0.45 |

The data in Table 1 show that the aminofulvene derivatives of this invention (Runs 10-17) are effective 3. The composition of claim 1 wherein the aminofulvene derivative has formula (i).

4. The composition of claim 3 wherein $R_1$-$R_4$ are all hydrogen.

5. The composition of claim 4 wherein $R_{11}$ is a methyl group.

6. The composition of claim 1 wherein the aminofulvene derivative has formula (ii).

7. The composition of claim 6 wherein $R_1$-$R_4$ are hydrogen.

8. The composition of claim 7 wherein $R_{11}$ is a methyl group.

9. A method for improving the antiknock performance of an internal combustion engine which comprises operating the engine on the composition of claim 1.

10. A gasoline composition comprising (a) a major amount of gasoline and (b) from about 25 to about 2,500 mg/liter of an aminofulvene derivative having any one of the following formulas:

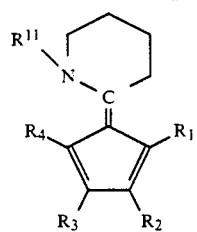
(i)

where $R_1$-$R_4$ are each hydrogen or an electron withdrawing group of the formula COOR$_8$, where $R_8$ is a hydrocarbyl group having from 1 to 2 carbon atoms, $R_{11}$ is an alkyl group having from 1 to 2 carbon atoms; or

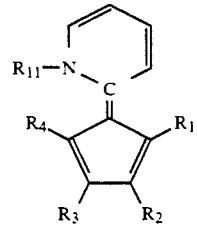
(ii)

where $R_1$-$R_4$ and $R_{11}$ are defined as in (i) above.

11. The composition of claim 10 wherein the aminofulvene derivative has formula (i).

12. The composition of claim 10 wherein the aminofulvene derivative has formula (ii).

13. A fuel concentrate comprising (a) from about 10 to about 70 wt. % of at least one of the following aminofulvene derivatives

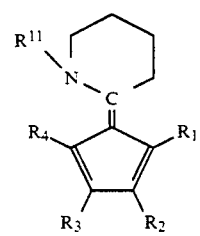
(i)

where $R_1$-$R_4$ are hydrogen or an electron withdrawing group of the formula COOR$_8$, where $R_8$ is a hydrocarbyl group having from 1 to 8 carbon atoms, $R_{11}$ is an alkyl group having from 1 to 8 carbon atoms; or

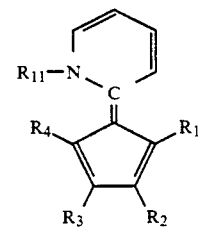
(ii)

where $R_1$-$R_4$ and $R_{11}$ are defined as in (i) above, and (b) from about 30 to about 90 wt. % of a hydrocarbon solvent, an alcohol solvent, or mixtures thereof boiling in the range of from about 150° to about 400° F.

14. The concentrate of claim 13 wherein the hydrocarbon solvent comprises an aromatic hydrocarbon solvent.

* * * * *